United States Patent [19]  [11]  4,424,075
Schmidt  [45]  Jan. 3, 1984

[54] IMPREGNATING COMPOSITIONS FOR CELLULOSE CONTAINING MATERIALS

[75] Inventor: Werner Schmidt, Augustin, Fed. Rep. of Germany

[73] Assignee: Dynamit Nobel AG, Troisdorf, Fed. Rep. of Germany

[21] Appl. No.: 351,423

[22] Filed: Feb. 23, 1982

[30] Foreign Application Priority Data

Feb. 24, 1981 [DE] Fed. Rep. of Germany ....... 3106748

[51] Int. Cl.$^3$ .......................... C09K 3/00; C08G 2/00
[52] U.S. Cl. .......................... 106/287.12; 106/287.17; 528/12; 528/16; 528/19
[58] Field of Search ...................... 106/287.12, 287.17; 536/463; 528/12, 19, 16

[56] References Cited

U.S. PATENT DOCUMENTS 2,729,572  1/1956  Torkelson ...................... 106/287.12

OTHER PUBLICATIONS

Chem. Abst. 52:13,662h, Kreshkov, 1958.
Chem. Abst. 52:17,637d, Khanan, 1958.

Primary Examiner—Theodore Morris
Attorney, Agent, or Firm—Felfe & Lynch

[57] ABSTRACT

Agent for impregnating materials that contain cellulose, mainly paper and wood. The active ingredient is a mixture of alkali aluminate and alkyl silanols that exhibits an intense hydrophobing effect at low concentrations. The agent can be employed in aqueous solution, e.g. in an enclosed space without the special exhaust devices required with volatile solvents. The solution is storage-stable. It contains preferably between 0.1 and 2.0% by weight of alkyl silanol and between 0.03 and 0.1% by weight of alkali aluminate.

9 Claims, No Drawings

IMPREGNATING COMPOSITIONS FOR CELLULOSE CONTAINING MATERIALS

This invention relates to a new composition for impregnating cellulose containing materials, to make them water-repellent. The active ingredient of the composition comprises hydrolysis products of certain silanes mixed with an aluminate liquor.

The addition of alkyl silanes to materials that contain cellulose to make them hydrophobic is known. The known method requires relatively concentrated solutions of up to 10% or more, for example, in alcohol and still does not result in completely satisfactory water resistance. Adding certain esters of metallic acids to these solutions of silanes in alcohol to improve hydrophobing is therefore also known. The disadvantage of doing so, however, is that the alcohol solution must contain relatively high concentrations of the materials to obtain satisfactory results. The presence of alcohol as a solvent also increases the risk of fire and requires supplementary exhaust devices to be installed when the process is conducted in an enclosed space.

There has thus been a need for an agent that can be used to hydrophobe materials that contain cellulose, that will be maximally effective at even low concentrations, and that can be employed in a solvent that will not make for any problems.

The present invention provides a hydrophobing agent for cellulose containing materials comprising an aqueous or aqueous alcohol solution of alkali aluminate and alkyl silanols (with the alkyl being ethyl, propyl, or n-butyl). Even a 0.2% solution of such a mixture in water will exhibit a hydrophobing effect. Surprisingly enough, however, while neither an aqueous solution of a silanol nor an aluminate solution will by itself impregnate the material in question, a mixture of the two components will have this desired effect.

To make the cellulose-containing material hydrophobic in accordance with the invention it can be immersed in the impregnating agent and then dried. It is however also possible to treat the material to be impregnated by brushing, dabbing, or spraying it with the agent. It will not be necessary to subsequently subject the material being treated to hours or days or damping storage to ensure satisfactory impregnation as is sometimes recommended when a solution of a silane in alcohol is employed. When the impregnation and hydrophobing agent in accordance with the invention is employed, the material that has been impregnated will be completely water resistant as soon as it dries and can be used immediately.

The impregnating agent in accordance with the invention can be used to make pure cellulose as well as cellulose in all its natural and synthetic variations and processed forms hydrophobic. Pure cellulose shall be understood to mean paper, including filter paper and cellulose fiber, for example, while variations and processed forms shall be understood to mean products like cardboard, wood, particle board, and cotton cloth or fabric. The new impregnating agent is especially appropriate for making all processed forms of paper hydrophobic and for impregnating wood.

The alkyl groups of the alkyl silanols in the solution in accordance with the invention are either the ethyl, propyl, or n-butyl group. Other alkyl groups will not provide stable aqueous or aqueous alcohol solutions. The production of such solutions is specified in German Patent . . . (Application P 3 037 220.4), to which the reader is referred for details. Generally, production involves dissolving the appropriate alkyl trialkoxysilanes in slightly acidified water and then distilling off the alcohol that occurs in hydrolysis if necessary. Preferred alkoxy groups in these alkyl trialkoxysilanes are those with 1 to 4 carbon atoms. The alkoxy groups of the alkyl trialkoxysilane in the aqueous or aqueous alcohol solutions obtained in this hydrolysis are largely hydrolyzed, and the alkyl silane will occur in the solution primarily in the form of alkyl trihydroxysilane. In accordance with the invention, however, solutions in which only one or two of the alkoxy groups of the alkyl trialkoxysilane have been converted into hydroxyl groups can also be employed.

Some of the silanol groups may also occur in partially condensed form with Si-O-Si groups, especially if the aqueous solutions have been standing for very long. This partial condensate should however contain no more than 10 Si-O-Si units per molecule. Such a partial condensation will take place especially when concentrated solutions are employed as preferred.

The solutions in accordance with the invention will preferably contain from 0.1 to 2.0% by weight of alkyl silanol, with from 0.3 to 1.0% by weight being especially preferred. Between 0.03 and 1.0% by weight and preferably between 0.1 and 0.4% by weight of the alkali aluminate will be employed. Concentrated solutions can also be employed, although they will generally result in no increase in the hydrophobing effect.

The ratio by weight of alkyl silanol to alkali aluminate may vary widely from 1:1:0 to 10:1, with from 3.5 to 6 parts of alkali aluminate to 10 parts of alkyl silanol preferred.

Especially appropriate alkali aluminates are sodium and potassium aluminate, with the sodium preferred.

The aqueous solution of the alkyl silanol may if necessary also contain alcohol deriving from the hydrolysis of the corresponding alkyl trialkoxysilane. This alcohol will not usually have to be distilled off. The preferred solution should contain no more than 5% by weight of it and generally between 1 and 3% by weight in terms of the solution. In concentrated silanol solutions, the alcohol content of the impregnation solutions in accordance with the invention can even increase to 10% by weight.

EXAMPLE 1

Producing a solution of silanol 10 g of propyl trimethoxysilane were stirred at room temperature with 90 g of water, to which 2 drops of 1% HCl had been added, until in a few minutes a clear solution developed. The finished solution theoretically contained in addition to the alcohol separated in hydrolysis 7.4 g of propyl silanetriol.

This solution will be designated "Solution A" in what follows.

The sodium aluminate solution was a commercially available 50% product that will be designated "Solution B."

EXAMPLE 2

Reference example 25 g of Solution A were diluted with water to 100 g. Pieces of filter paper (Schleicher & Schüll No. 1375) measuring 10×15 cm were immersed for 30 seconds in this solution, dried overnight, and placed on a sheet of glass for a drip test. 0.5 cm$^2$ of water were dripped onto the filter paper. The drop was covered with a watch glass to keep the observed duration of absorption from being contaminated by air drying. This precaution was however unnecessary in the present case because the drop was immediately absorbed by the paper.

The same results were obtained when 5 or 50 g of Solution A were employed as above.

When 84 g/m² soda kraft paper was employed instead of filter paper, the same results were obtained.

EXAMPLE 3

Another reference example 0.25 g of Solution B were diluted with water to 100 g. The same type of filter paper employed in Example 2 was immersed for 30 seconds, dried overnight, and placed on a sheet of glass for the drip test. 0.5 cm² of water were dripped onto the filter paper and evaluated as in Example 2. The drop of water was immediately absorbed.

When the concentration of Solution B was doubled to 0.5 g in a total solution of 100 g, the results were the same. Only when the concentration was doubled again to 1.0 g in a total of 100 g was the drop absorbed, not instantaneously, but within 30 seconds.

Similar results were obtained when sodium kraft paper was used as in Example 2 instead of filter paper.

EXAMPLE 4

The impregnation of paper 5 g of Solution A were diluted with 94.5 g of water and added to 0.5 g of Solution B. Sheets of filter paper and sodium kraft paper were immersed in this mixture as in Example 2, dried, and tested with 0.5 cm² of water as in Example 2. The drop remained unabsorbed for several hours, evaporating in spite of being covered after about 50 hours. When the concentration was reduced by one half to 2.5 g of Solution A and 0.25 g of Solution B in 100 g of impregnation solution, the same extremely satisfactory hydrophobing effect was obtained.

EXAMPLE 5

The effects of sodium aluminate

The same procedure as in Example 4 was followed, with 5 g of Solution A and, in 100 g of the impregnation solution, the following varying amounts of Solution B:
(1) 0.5 g
(2) 0.25
(3) 0.125
(4) 0.06.

The water-drop test as in Example 2 revealed that each of these solutions produced very satisfactory hydrophobing results. None of the water was absorbed by the paper, but evaporated in about 50 hours.

EXAMPLE 6

The hydrophobing of wood

The test samples were 15×15 cm sheets of 12 mm-thick laminated limba wood. The samples were immersed in the solution being tested and brushed with it for 1 minute. They were then dried overnight and tested like the paper in the foregoing examples.

The table shows the results of the test for various concentrations.

| Content of active ingredient in 100 g of impregnation solution | | |
|---|---|---|
| Solution A | Solution B | Results |
| 2.5 g | 0.25 g | Drop absorbed in about 1 hour. |
| 5.0 | 0.5 | Drop unabsorbed. |
| 12.5 | 1.25 | Drop unabsorbed. |
| 1.25 | 0.12* | Drop absorbed in about ½ hour. |

*Blank

It will be understood that the specification and examples are illustrative but not limitative of the present invention and that other embodiments within the spirit and scope of the invention will suggest themselves to those skilled in the art.

What is claimed is:

1. Composition for impregnating cellulose-containing materials, which composition comprises an aqueous or aqueous alcohol solution of a mixture of an alkali aluminate and at least one alkyl silanol wherein the alkyl is selected from ethyl, propyl and n-butyl.

2. Composition as claim in claim 1, wherein the ratio of the alkali aluminate to alkyl silanols in said mixture is from 1:10 to 10:1.

3. Composition as claimed in claim 1 containing from 0.03% to 1.0% by weight of alkali aluminate and from 0.1 to 2.0% by weight of alkyl silanol.

4. Composition as claimed in claim 1, wherein the alkyl silanol is ethyl silanol.

5. Composition as claimed in claim 1, wherein the alkyl silanol is propyl silanol.

6. Composition as claimed in claim 1, wherein the alkyl silanol is n-butyl silanol.

7. Composition as claimed in claim 1, wherein a mixture of alkyl silanols is used in conjunction with said alkali aluminate.

8. Composition as claimed in claim 1, wherein the alkali aluminate is sodium aluminate.

9. Composition as claimed in claim 1, wherein said alkali aluminate is potassium aluminate.

* * * * *